United States Patent
Gedouin et al.

(12)

(10) Patent No.: US 6,596,288 B2
(45) Date of Patent: Jul. 22, 2003

(54) USE OF STEROLS AS ACTIVE INGREDIENT IN A COSMETIC COMPOSITION AGAINST ADIPOSITY

(75) Inventors: Antoine Gedouin, Saint Coulomb (FR); Romuald Vallee, St Meloir des Ondes (FR); Pierre-Yves Morvan, Rennes (FR)

(73) Assignee: Codif International SA, Saint Malo (FR)

( * ) Notice: Subject to any disclaimer, the term of this patent is extended or adjusted under 35 U.S.C. 154(b) by 0 days.

(21) Appl. No.: 09/997,270

(22) Filed: Nov. 30, 2001

(65) Prior Publication Data

US 2002/0106389 A1 Aug. 8, 2002

(30) Foreign Application Priority Data

Nov. 30, 2000 (FR) .............................................. 00 15549

(51) Int. Cl.$^7$ .......................... A61K 7/00; A61K 35/78; A61K 31/56
(52) U.S. Cl. ...................... 424/401; 424/776; 424/725; 514/182; 514/909
(58) Field of Search ................................. 424/401, 776, 424/725; 514/182, 909

(56) References Cited

U.S. PATENT DOCUMENTS 5,728,393 A * 3/1998 Soudant et al.

OTHER PUBLICATIONS

Pyrek, J. 4–Beta–Methyl Sterol from Marigold Flowers, abstract, AN 1969:68620, (1969).*

* cited by examiner

Primary Examiner—Russell Travers
Assistant Examiner—Shengjun Wang
(74) Attorney, Agent, or Firm—Armstrong, Westerman & Hattori, LLP

(57) ABSTRACT

The present invention relates to the use of sterols derived from a plant or algae extract as the active principle of a cosmetic composition for combating adiposity. Said sterols are, for example, at least one of the three following sterols: campesterol, beta-sitosterol or stigmasterol.

5 Claims, No Drawings

USE OF STEROLS AS ACTIVE INGREDIENT IN A COSMETIC COMPOSITION AGAINST ADIPOSITY

This application claims foreign priority of French application 00/15549, filed Nov. 30, 2000.

The present invention relates to a use of sterols as active principle in a cosmetic composition to combat adiposity and thus refine the silhouette.

Sterols are known for their use as active substance in anti-inflammatory medications in which they act as inhibitors of lipoxygenase. One may refer to the patent document FR-A-2 705 030 which shows such an activity.

They are also known for cosmetic compositions for treatment of the skin in which they act as emollients by presenting good properties of moisturizing and barrier. Document U.S. Pat. No. 4,604,281 shows such a use.

Concerning cosmetic compositions to combat adiposity, one is acquainted with those of which the active principles used present a lipolytic activity by which they stimulate the degradation (or lysis) of the fats stored in the human adipocytes, in particular in the form of triglycerides, and promote the elimination of the products of that degradation, in particular fatty acids and glycerols. For example, theophylline and isoproterenol are known to stimulate the lipolysis of triglycerides, in particular triglycerides of human adipocytes.

Moreover, in the French patent document No. 98 02152, the active principle used to stimulate lypolysis is a pyrone group which has the effect of activating the phosphorylation of a lipase enzyme for the degradation of the triglycerides in fatty acids. This pyrone group is, for example, mangosteen extracted from a tree of the *Garcinia mangostana* species.

One is also acquainted with cosmetic compositions the active principle of which is not to stimulate the lipolysis of triglycerides of human adipocytes but to inhibit the lipogenesis of these triglycerides.

It is to be recalled here that, in the adipocytes, lipolysis is in competition with lipogenesis which consists in the formation of fats, in particular triglycerides, and which brings into play an entire series of biochemical reactions bringing about the action of proteins with enzymatic activity such as Acyl-CoA synthetase and fatty acid synthetase, which are also known under the name FAS (fatty acid synthase).

Cerulenine is a compound which is known to inhibit lipogenesis by inhibition of the FAS synthetase.

In a previous patent application, it was also shown that the same is true with eicosapentanoic acid (EPA).

It has now been discovered that sterols which come from a plant or algae extract have, on the one hand, an inhibitory activity for lipogenesis of triglycerides produced by human adipocytes and, on the other hand, an activity stimulating the lipolysis of the same substances.

The invention therefore has as object the use of sterols from a plant or algae extract as active substance in a cosmetic composition to combat adiposity.

It is thought that the sterols that are contained in the said extract are responsible for an inhibitory effect on the action of an enzyme that plays a part in lipogenesis, in particular the synthesis of fatty acids by fatty acid synthetase FAS. Thus, by using a cosmetic composition that contains sterols as active principle, the lipogenesis of these fatty acids is inhibited or at the very least limited and their concentration in the adipocytes is thus reduced.

We were able to show below that most particularly campsterol and beta-sitosterol, generally present in plants or algae, have this inhibitory action.

It is to be understood that the cosmetic compositions that are planned to inhibit this lipogenesis make it possible to avoid the instantaneous recovery of the fat lost after lipolysis.

It is also thought that the sterols have a direct effect on the lipolysis of the triglycerides of human adipocytes by stimulating it.

We were able to show below that this is particularly true concerning the stigmasterol derived from a plant or algae extract.

It is to be understood that the cosmetic compositions that are planned to stimulate lipolysis have a direct curative effect by reducing excess fat.

It is also thought that sterols have an inhibitory effect on the differentiation of adipocytes. In fact, it has been demonstrated that steroid hormones (estrogens and androgens) regulate the differentiation of adipocytes, that is to say the maturation of dermic cells (fibroblasts) into cells capable of accumulating fat in the form of triglycerides.

Moreover, androgens such as testosterone, dihydrotestosterone (DHT), dehydroepiandrosterone (DHEA), androstanediol and androstenediol have an inhibitory effect on the differentiation of adipocytes, in particular by the inhibition of the activity of the enzyme glucose-6 phosphate dehydrogenase, while the action of the estrogens like beta-estradiol is expressed by a modulation of the expression of receptors like that of IGF1 (insulin growth factor 1).

During differentiation, the size of the cells and the fat content increase greatly, and "markers" also appear, such as, for example, an increase in expression of enzymes like lipoprotein lipase (LPL), a decrease in enzymatic activity like that of glycerol 3-phosphate dehydrogenase, an increase in the expression of membrane proteins like the fatty acid transporter (FAT), an increase in the expression of transcription factors of the genes of lipogenesis like the peroxisome proliferator-activated receptors (PPARs) or the CCAAT/enhancer-binding proteins (C/EBPs), and an increase in the quantity of intracellular proteins like p18 (INK4c), p21 (Waf1) or aP2 (adipocyte fatty acid binding protein or FABP).

It may therefore be thought that the effect of phytosterols is expressed by an effect on the differentiation of pre-adipocytes into adipocytes (anti-adipogenic effect), in addition to the inhibitory effect on lipogenesis and the lipolytic effect.

The cosmetic compositions that are planned for inhibiting the differentiation of adipocytes will have a preventive effect by preventing the development of excesses of fat.

According to the present invention, the extract containing at least one sterol is an oily extract obtained from seeds of *Polygonum fagopyrum*.

The present invention also relates to a preparation process of a substance that contains as active principle a lipidic extract of plants or algae containing sterols.

We will now describe the procedure of the experiments that were conducted to prove the effect of sterols derived from an extract of plants or algae on lipids.

In these experiments, adipocytes were isolated from abdominal restorative surgeries sampled in women. The experiment took place the day of the sampling. Fragments of adipose tissues were incubated for 30 minutes at 37° C. in the presence of collagenase, then the isolated adipocytes were washed and taken up in medium MEM buffered with bicarbonate, in the presence of antibiotics (penicillin/streptomycin), glutamine (2 mM), and delipidated bovine serum albumin (0.5%).

The tests concerning the effect on lipogenesis were then conducted in the following manner.

Adipocytes (90 μl of ¼ diluted suspension) were incubated for 1 hour, either with a control medium (4 hours), with molecules known to inhibit the neosynthesis of fatty acids (EPA), as for example insulin, or with previously diluted extracts (added under 100 μl).

As to the sterols and to the lipidic extracts of plants or algae, they were diluted in mineral oil which has been verified to not inhibit incorporation or extraction of adipocyte lipids. Then, 10 μl of [$2^{14}$C]-acetate, 50 μCi/ml, were added, and the samples were either cultivated at 37° C. in the presence of 5% $CO_2$ for 4 additional hours, or immediately frozen at −80° C. (control t0).

Each experiment was carried out in duplicate insofar as the test proved to be reproducible and with low standard deviations.

At the times indicated, the samples were frozen at −80° C. The lipids were then extracted according to the method of Bligh and Dyer (extraction methanol/chloroform/water), then dried under nitrogen. The radioactivity incorporated was then counted by liquid scintillation.

As to the tests concerning the effect on lipolysis, they were conducted in the following manner. Adipocytes (540 μl of suspension) were incubated for 2 hours in a water bath at 37° C., with agitation, in the presence of 60 μl of different sterols. The experiments were carried out in triplicate.

Then, the non-esterified fatty acids (AGNE) released by the adipocytes were determined in the sub-adipocyte media. The values obtained were treated by an analysis of variance (ANOVA) by means of the multiple comparison test of Dunnett. The values were considered as significant when the probability p was less than the threshold of significance 0.05.

The experimental results are recorded hereinafter.

Concerning the lipogenesis test, the acetate incorporation after 4 hours of labeling was great (control in Table 1 below, namely 208546 cpm in the absence of insulin) and the background at t0 was low: 646.5 cpm, namely 3% of the 4h time.

It is to be noted that the addition of insulin effectively increases the incorporation of acetate in human adipocytes (see the same results as in Table 1 but in the presence of insulin). As a matter of fact it is to be noted that the incorporation of acetate increased 16% in the presence of 1 nM of insulin (Table 2).

With another donor, the increase was 120% in the presence of 100 nM of insulin (result not shown).

It is to be noted that EPA (or eicosapentanoic acid) (C20:5) in oily solution (mineral oil) at the two concentrations tested (0.1 mM and 1 mM) greatly inhibited incorporation (82 and 97% inhibition respectively). It will be noted that in the presence of insulin (1 nM), the effect of the EPA at 0.1 mM is slightly decreased (62% instead of 82%) but it was still 97% at 1 mM EPA.

Three sterols were tested in the model described above: campesterol, beta-sitosterol, and stigmasterol. They were diluted in mineral oil the presence of which in the medium has been verified to not inhibit incorporation or extraction of the adipocyte lipids. As for EPA above, they were tested both in the absence and in the presence of insulin (1 nM).

In the first case, campesterol at 0.01, 0.1 and 1 mM inhibits in a dose-dependent way the incorporation of acetate with respect to the mineral oil control (Table 1). At the lowest concentration tested (10 μM), the inhibition is 8%. At 0.1 mM, the inhibition is 10% and, at 1 mM, it is 26%.

With beta-sitosterol at 1 mM, the inhibition of acetate incorporation is 16%. At 0.01 and 0.1 mM, this inhibition is weak and non-significant.

As to stigmasterol, at the three concentrations tested (0.01, 0.1 and 1 mM), the inhibition is weak and non-significant.

In the second case, in the presence of insulin (1 nM), campesterol at 0.01 mM had no significant effect. By contrast, at concentrations of 0.1 and 1 mM, it inhibits in a dose-dependent way the incorporation of acetate with respect to the mineral oil control (Table 2): the inhibition is 15% at 0.1 nM and 52% at 1 mM. Its inhibitory effect is therefore amplified by the presence of insulin.

It is therefore to be noted that campesterol regulates the synthesis of triglycerides induced by insulin.

Beta-sitosterol at 1 mM inhibits the incorporation of acetate by 17%. At 0.01 and 0.1 mM, it has no significant effect (inhibition less than 10%).

On the other hand, stigmasterol, at the three concentrations tested (0.01, 0.1 and 1 mM) had no significant effect (inhibition less than 5%).

We now study the same effects as previously but with two oily extracts obtained from seeds of *Polygonum fagopyrum* (sarrazin, buckwheat). One of these extracts, designated POL, is obtained by extraction with supercritical $CO_2$. It contains sterols (approximately 3.6%), in particular beta-sitosterol (78% of the sterols), campesterol (7%) and stigmasterol (2%). It was tested at 0.05, 0.2 and 0.5% (diluted in mineral oil).

As to the second extract which is a wax designated P, it is obtained by mixture of an extract of co-extraction with supercritical $CO_2$ in the presence of a vegetable oil (C8–C10TG) and of a second vegetable oil solid at ambient temperature, waxy oil, (C16–C18 TG). The wax obtained presents the advantage of being stable to oxidation (evaluation according to the Rancimat method). It was tested at 0.1, 0.5 and 2%.

Moreover, an excipient, designated MICRE, composed of the extraction solvent C8–C10 TG and the waxy oil C16–C18 TG, was tested.

As previously, these tests were done at first in the absence of insulin (see the results Table 1) and then in the presence of insulin (see the results Table 2).

In the absence of insulin, it can be noted that the POL extract greatly inhibits the incorporation of acetate: 74% inhibition at the concentration of 0.05%, and 91–92% inhibition at the concentrations of 0.2 and 0.5% (Table 1).

The P wax, tested at 0.1%, inhibits the incorporation of acetate by 18%. At 0.5%, it inhibits it by 33%. At the highest concentration tested (2%), it inhibits it by 68%. It is to be noted that at that concentration, the MICRE wax (without the sarrazin extract) inhibited it by 44%.

In the presence of insulin (1 nM), the POL extract greatly inhibited the incorporation of acetate: 49, 89 and 91% inhibition respectively at the concentrations of 0.05, 0.2 and 0.5% (Table 2).

The P wax, tested at 0.1%, had no significant effect (5% inhibition). At 0.5%, it inhibited the incorporation of acetate by 42%. At the highest concentration tested (2%), it inhibited it by 57%. At that concentration, the MICRE wax (without the sarrazin extract) inhibited it only by 20%.

We now discuss the tests on lipolysis.

It can be noted (see Table 3) that basal lipolysis was elevated, but cellular lysis at the end of the experiment was moderate. The reference molecules (theophylline at 1 nM and isoproterenol at 1 μM) stimulated the lipolysis (p<0.05).

Campesterol and beta-sitosterol, tested at $10^{-6}$ M, $10^{-5}$ M, $10^{-4}$ M, $10^{-3}$ M and $10^{-2}$ M, did not stimulate lipolysis under the experimental conditions of this test (Table 3).

Stigmasterol did not show significant effect at $10^{-6}$ M and at $10^{-2}$ M, but it stimulated in a significant way (p<0.05)

the liberation of NEFA (non-esterified fatty acids) (26% to 33% increase) at $10^{-5}$ M, $10^{-4}$ M and $10^{-3}$ M. This sterol therefore showed a lipolytic effect under the experimental conditions.

The conclusions to be drawn from these experiments are the following.

Campesterol and beta-sitosterol inhibit the incorporation of acetate by isolated human adipocytes. Their effect limits lipogenesis.

Stigmasterol increases the liberation of fatty acids by isolated human adipocytes. Its effect stimulates lipolysis.

The oily extract of seeds of *Polygonum fagopyrum* (POL), containing campesterol, beta-sitosterol and stigmasterol, decreases the incorporation of acetate by isolated human adipocytes.

The buckwheat wax (P wax), containing the extract of *Polygonum fagopyrum*, also decreases the incorporation of acetate, with an activity greater than that of the wax alone (without the POL extract).

TABLE 1

Effect of EPA, 3 sterols and oily extracts of sarrazin on the incorporation of acetate (LIPOGENESIS) in the absence of insulin

| Treatment | Average of cpm | cpm*- t0 test | % control | % inhibition |
|---|---|---|---|---|
| t0 test | 6465 | 0 | 0 | / |
| Control | 208546 | 202081 | 100 | / |
| EPA | | | | |
| 1 mM | 1287 | 6373 | 3 | 97 |
| 0.1 mM | 43253 | 36788 | 18 | 82 |
| Campesterol | | | | |
| $10^{-3}$ M | 156448 | 149983 | 74 | 26 |
| $10^{-4}$ M | 188278 | 181813 | 90 | 10 |
| $10^{-5}$ M | 191817 | 185352 | 92 | 8 |
| Beta-sitosterol | | | | |
| $10^{-3}$ M | 175711 | 169246 | 84 | 16 |
| $10^{-4}$ M | 198694 | 192229 | 95 | 5 |
| $10^{-5}$ M | 200044 | 193579 | 96 | 4 |
| Stigmasterol | | | | |
| $10^{-3}$ M | 210055 | 203590 | 101 | 0 |
| $10^{-4}$ M | 200467 | 194002 | 96 | 4 |
| $10^{-5}$ M | 198442 | 191977 | 95 | 5 |
| POL | | | | |
| 0.5% | 24665 | 18200 | 9 | 91 |
| 0.2% | 23153 | 16688 | 8 | 92 |
| 0.05% | 58489 | 52024 | 26 | 74 |
| P Wax | | | | |
| 2% | 71676 | 65211 | 32 | 68 |
| 0.5% | 141501 | 135036 | 67 | 33 |
| 0.1% | 172219 | 165754 | 82 | 18 |
| MICRE | | | | |
| 2% | 120314 | 113849 | 56 | 44 |

*cpm = counts per minute

TABLE 2

Effect of EPA, 3 sterols and oily extracts of sarrazin on the incorporation of acetate (LIPOGENESIS) in the presence of insulin (1 nM)

| Treatment | Average of cpm* | cpm*- t0 test | % control | % inhibition |
|---|---|---|---|---|
| t0 test | 6465 | 0 | 0 | / |
| Control | 241167 | 234702 | 100 | / |
| EPA | | | | |
| 1 mM | 13384 | 6919 | 3 | 97 |
| 0.1 mM | 96244 | 89779 | 38 | 62 |
| Campesterol | | | | |
| $10^{-3}$ M | 119960 | 113495 | 48 | 52 |
| $10^{-4}$ M | 206655 | 200190 | 85 | 15 |
| $10^{-5}$ M | 243051 | 236586 | 101 | 0 |
| Beta-sitosterol | | | | |
| $10^{-3}$ M | 201168 | 194703 | 83 | 17 |
| $10^{-4}$ M | 224445 | 217980 | 93 | 7 |
| $10^{-5}$ M | 216417 | 209952 | 89 | 11 |
| Stigmasterol | | | | |
| $10^{-3}$ M | 227385 | 220920 | 94 | 6 |
| $10^{-4}$ M | 234524 | 228059 | 97 | 3 |
| $10^{-5}$ M | 235529 | 229064 | 98 | 2 |
| POL | | | | |
| 0.5% | 27264 | 20799 | 9 | 91 |
| 0.2% | 32221 | 25756 | 11 | 89 |
| 0.05% | 125449 | 118984 | 51 | 49 |
| P Wax | | | | |
| 2% | 106660 | 100195 | 43 | 57 |
| 0.5% | 143077 | 136612 | 58 | 42 |
| 0.1% | 228281 | 221816 | 95 | 5 |
| MICRE | | | | |
| 2% | 194695 | 188230 | 80 | 20 |

*cpm = counts per minute

TABLE 3

Effects of 3 sterols on the liberation of NEFA (non-esterified fatty acids) (LIPOLYSIS)

| Treatment | Average of the NEFA (μM) | Standard Deviation | % Control | p |
|---|---|---|---|---|
| Untreated | 141 | 12 | 100 | — |
| Theophylline | | | | |
| 1 mM | 551 | 10 | 390 | P < 0.01 |
| Isoproterenol | | | | |
| 1 μM | 483 | 28 | 342 | P < 0.01 |
| Campesterol | | | | |
| $10^{-2}$ M | 167 | 14 | 118 | p > 0.05 |
| $10^{-3}$ M | 138 | 8 | 98 | p > 0.05 |
| $10^{-4}$ M | 155 | 6 | 109 | p > 0.05 |
| $10^{-5}$ M | 140 | 14 | 99 | p > 0.05 |
| $10^{-6}$ M | 166 | 15 | 117 | p > 0.05 |
| Beta-sitosterol | | | | |
| $10^{-2}$ M | 131 | 17 | 92 | p > 0.05 |
| $10^{-3}$ M | 145 | 11 | 103 | p > 0.05 |
| $10^{-4}$ M | 135 | 19 | 96 | p > 0.05 |
| $10^{-5}$ M | 151 | 2 | 107 | p > 0.05 |
| $10^{-6}$ M | 156 | 13 | 110 | p > 0.05 |
| Stigmasterol | | | | |
| $10^{-2}$ M | 158 | 3 | 112 | p > 0.05 |
| $10^{-3}$ M | 178 | 10 | 126 | p < 0.05 |
| $10^{-4}$ M | 189 | 14 | 133 | p < 0.01 |
| $10^{-5}$ M | 180 | 21 | 128 | p < 0.05 |
| $10^{-6}$ M | 158 | 15 | 112 | p > 0.05 |

What is claimed is:

1. Method for combating adiposity comprising administering a cosmetic composition comprising a sterol-containing plant or algae extract as active principle of the cosmetic composition, wherein said extract is an oily extract obtained from seeds of *Polygonum fagopyrum*.

2. Method according to claim 1, wherein said extract comprises at least one of the three following sterols: campesterol, beta-sitosterol or stigmasterol.

3. Method according to claim 2, wherein said extract comprises at least one of the two following sterols: campesterol or beta-sitosterol, said cosmetic composition being planned to combat adiposity by inhibition of lipogenesis by adipocytes.

4. Method according to claim 2, wherein said extract comprises at least stigmasterol, said cosmetic composition being planned to combat adiposity by stimulation of lipolysis by adipocytes.

5. Method according to claim 2, wherein said cosmetic composition is planned to combat adiposity by inhibition of differentiation of pre-adipocytes into mature adipocytes.

* * * * *